United States Patent [19]
Laffend et al.

[11] Patent Number: 6,025,184
[45] Date of Patent: Feb. 15, 2000

[54] BIOCONVERSION OF A FERMENTABLE CARBON SOURCE TO 1,3-PROPANEDIOL BY A SINGLE MICROORGANISM

[75] Inventors: Lisa Anne Laffend; Vasantha Nagarajan, both of Wilmington; Charles Edwin Nakamura, Claymont, all of Del.

[73] Assignees: E. I. du Pont de Nemours and Company, Wilmington, Del.; Genencor International Inc., Palo Alto, Calif.

[21] Appl. No.: 08/966,794

[22] Filed: Nov. 10, 1997

Related U.S. Application Data

[62] Division of application No. 08/440,293, May 12, 1995, Pat. No. 5,686,276.

[51] Int. Cl.$^7$ .................................................. C12N 1/20
[52] U.S. Cl. ............................ 435/252.33; 435/252.3; 435/320.1
[58] Field of Search .......................... 435/320.1, 252.3, 435/252.33; 536/23.1

[56] References Cited

FOREIGN PATENT DOCUMENTS

| 0 361 082 | 4/1990 | European Pat. Off. |
| 0 373 230 | 6/1990 | European Pat. Off. .......... C12P 7/18 |
| 3734 764 | 10/1987 | Germany . |
| WO-A-91 15590 | 10/1991 | WIPO . |
| WO-A-93 25696 | 12/1993 | WIPO . |

OTHER PUBLICATIONS

Tong et al. Applied and Environmental Microbiology, vol. 57, No. 12, pp. 3541–3546, Dec. 1991.

Daniel Rolf et al., "Growth Temperature–Dependent Activity of Glycerol Dehydratase in *Escherichia Coli* Expressing the *Citrobacter Freundii* dha Regulon", *Chemical Abstracts*, vol. 118, No. 7, Feb. 15, 1993.

Tong, I Teh et al., "1,3–Propanediol Production by *Escherichia Colli* Expressing Genes from the *Klebsiella Pneumoniae* dha Regulon", *Chemical Abstracts*, vol. 116, No. 9, Mar. 2, 1992.

Otto, Karin Elizabeth, "Cloning and Characterization of the Propanediol Dehydratase Genes in *Salmonella Typhimurium*", *Chemical Abstracts*, vol. 120, No. 11, Mar. 14, 1994.

Boenigk, Rainer et al., "Fermentation of Glycerol to 1,3–Propanediol in Continuous Cultures of *Citrobacter Freundii*", *Chemical Abstracts*, vol. 118, No. 17, Apr. 26, 1993.

Veiga da Cunha et al., *J. Bacteriol*, 174(3), 1013–1019, 1992.

Tong, I–T et al., *Appl. Biochem. Biotech.*, 34/35, 149–159, 1992.

Tong, I–T., Ph.D.,, Thesis, *University of Wisconsin–Madison*, partial text submitted; full text provided upon request, 1992.

Steib, M. et al. *Arch. Microbiol.*, 140 139 146 (1984).

Talarico, T. L. et al., *Applied and Environmental Microbiology*, Apr. 1990 pp. 943–948.

Daniel, R. et al., *J. of Bacteriology*, 177(8), 2151–2156(1995).

Tobinatsu, T. et al., *J. Biolog. Chem.*, 270(13), 7142–7148(1995).

Ruch, F. E. et al., *J. Bacteriol.*, 124(1), 348–352(1975).

Sobolov, M. et al, 79, 261–266.

*Primary Examiner*—James Ketter
*Assistant Examiner*—Irem Yucel

[57] ABSTRACT

A process is provided for the bioconversion of a carbon substrate to 1,3-propanediol by a single organism utilizing either microorganisms containing the genes encoding for an active glycerol or diol dehydratase enzyme by contacting these organisms with a carbon substrate under the appropriate fermentation conditions.

4 Claims, 2 Drawing Sheets

BIOCONVERSION OF A FERMENTABLE CARBON SOURCE TO 1,3-PROPANEDIOL BY A SINGLE MICROORGANISM

This is a division of application Ser. No. 08/440,293, filed May 12, 1995, now U.S. Pat. No. 5,686,286, issued Nov. 11, 1997.

FIELD OF INVENTION

This invention comprises a process for the bioconversion of a fermentable carbon source to 1,3-propanediol by a single microorganism.

BACKGROUND 1,3-Propanediol is a monomer having potential utility in the production of polyester fibers and the manufacture of polyurethanes and cyclic compounds.

A variety of chemical routes to 1,3-propanediol are known. For example ethylene oxide may be converted to 1,3-propanediol over a catalyst in the presence of phosphine, water, carbon monoxide, hydrogen and an acid, by the catalytic solution phase hydration of acrolein followed by reduction, or from hydrocarbons such as glycerol, reacted in the presence of carbon monoxide and hydrogen over catalysts having atoms from group VIII of the periodic table. Although it is possible to generate 1,3-propanediol by these methods, they are expensive and generate waste streams containing environmental pollutants.

It has been known for over a century that 1,3-propanediol can be produced from the fermentation of glycerol. Bacterial strains able to produce 1,3-propanediol have been found, for example, in the groups *Citrobacter, Clostridium, Enterobacter, Ilyobacter, Klebsiella, Lactobacillus,* and *Pelobacter.* In each case studied, glycerol is converted to 1,3-propanediol in a two step, enzyme catalyzed reaction sequence. In the first step, a dehydratase catalyzes the conversion of glycerol to 3-hydroxypropionaldehyde (3-HP) and water, Equation 1. In the second step, 3-HP is reduced to 1,3-propanediol by a NAD$^+$-linked oxidoreductase, Equation 2. The 1,3-propanediol is not metabolized further and, as a result,

Glycerol→3-HP+H$_2$O          (Equation 1)

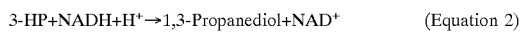

3-HP+NADH+H$^+$→1,3-Propanediol+NAD$^+$     (Equation 2)

accumulates in high concentration in the media. The overall reaction consumes a reducing equivalent in the form of a cofactor, reduced β-nicotinamide adenine dinucleotide (NADH), which is oxidized to nicotinamide adenine dinucleotide (NAD$^+$).

The production of 1,3-propanediol from glycerol is generally performed under anaerobic conditions using glycerol as the sole carbon source and in the absence of other exogenous reducing equivalent acceptors. Under these conditions, in e.g., strains of *Citrobacter, Clostridium,* and *Klebsiella,* a parallel pathway for glycerol operates which first involves oxidation of glycerol to dihydroxyacetone (DHA) by a NAD$^+$- (or NADP$^+$-) linked glycerol dehydrogenase, Equation 3. The DHA, following phosphorylation to dihydroxyacetone phosphate (DHAP) by a DHA kinase (Equation 4),

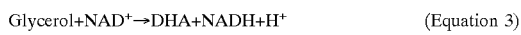

Glycerol+NAD$^+$→DHA+NADH+H$^+$    (Equation 3)

DHA+ATP→DHAP+ADP          (Equation 4)

becomes available for biosynthesis and for supporting ATP generation via e.g., glycolysis. In contrast to the 1,3-propanediol pathway, this pathway may provide carbon and energy to the cell and produces rather than consumes NADH.

In *Klebsiella pneumoniae* and *Citrobacter freundii,* the genes encoding the functionally linked activities of glycerol dehydratase (dhaB), 1,3-propanediol oxido-reductase (dhaT), glycerol dehydrogenase (dhaD), and dihydroxyacetone kinase (dhaK) are encompassed by the dha regulon. The dha regulons from *Citrobacter* and *Klebsiella* have been expressed in *Escherichia coli* and have been shown to convert glycerol to 1,3-propanediol.

Biological processes for the preparation of glycerol are known. The overwhelming majority of glycerol producers are yeasts but some bacteria, other fungi and algae are also known. Both bacteria and yeasts produce glycerol by converting glucose or other carbohydrates through the fructose-1,6-bisphosphate pathway in glycolysis or the Embden Meyerhof Parnas pathway, whereas, certain algae convert dissolved carbon dioxide or bicarbonate in the chloroplasts into the 3-carbon intermediates of the Calvin cycle. In a series of steps, the 3-carbon intermediate, phosphoglyceric acid, is converted to glyceraldehyde 3-phosphate which can be readily interconverted to its keto isomer dihydroxyacetone phosphate and ultimately to glycerol. Although biological methods of both glycerol and 1,3-propanediol production are known, it has never been demonstrated that the entire process can be accomplished by a single organism.

Neither the chemical nor biological methods described above for the production of 1,3-propanediol is well suited for industrial scale production since the chemical processes are energy intensive and the biological processes require the expensive starting material, glycerol. A method requiring low energy input and an inexpensive starting material is needed. A more desirable process would incorporate a microorganism that would have the ability to convert basic carbon sources such as carbohydrates, or sugars to the desired 1,3-propanediol end-product.

Although a single organism conversion of fermentable carbon source other than glycerol or dihydroxyacetone to 1,3-propanediol would be desirable, it has been documented that there are significant difficulties to overcome in such an endeavor. For example, Gottschalk et al. (EP 373 230) teach that the growth of most strains useful for the production of 1,3-propanediol, including *Citrobacter freundii, Clostridium autobutylicum, Clostridium butylicum,* and *Klebsiella pneumoniae,* is disturbed by the presence of a hydrogen donor such as fructose or glucose. Strains of *Lactobacillus brevis* and *Lactobacillus buchner,* which produce 1,3-propanediol in co-fermentations of glycerol and fructose or glucose, do not grow when glucose is provided as the sole carbon source, and, although it has been shown that resting cells can metabolize glucose or fructose, they do not produce 1,3-propanediol. (Veiga DA Cunha et al., *J. Bacteriol.* 174, 1013 (1992)). Similarly, it has been shown that a strain of *Ilyobacter polytropus,* which produces 1,3-propanediol when glycerol and acetate are provided, will not produce 1,3-propanediol from carbon substrates other than glycerol, including fructose and glucose. (Steib et al., *Arch. Microbiol.* 140, 139 (1984)). Finally Tong et al. (*Appl. Biochem. Biotech.* 34, 149 (1992)) has taught that recombinant *Escherichia coli* transformed with the dha regulon encoding glycerol dehydratase does not produce 1,3-propanediol from either glucose or xylose in the absence of exogenous glycerol.

Attempts to improve the yield of 1,3-propanediol from glycerol have been reported where co-substrates capable of providing reducing equivalents, typically fermentable sugars, are included in the process. Improvements in yield have been claimed for resting cells of *Citrobacter freundii* and *Klebsiella pneumoniae* DSM 4270 cofermenting glycerol and glucose (Gottschalk et al., supra.; and Tran-Dinh et al., DE 3734 764); but not for growing cells of *Klebsiella pneumoniae* ATCC 25955 cofermenting glycerol and glucose, which produced no 1,3-propanediol (I-T. Tong, Ph.D. Thesis, University of Wisconsin-Madison (1992)). Increased yields have been reported for the cofermentation of glycerol and glucose or fructose by a recombinant *Escherichia coli;* however, no 1,3-propanediol is produced in the absence of glycerol (Tong et al., supra.) . In these systems, single organisms use the carbohydrate as a source of generating NADH while providing energy and carbon for cell maintenance or growth. These disclosures suggest that sugars do not enter the carbon stream that produces 1,3-propanediol. In no case is 1,3-propanediol produced in the absence of an exogenous source of glycerol. Thus the weight of literature clearly suggests that the production of 1,3-propanediol from a carbohydrate source by a single organism is not possible.

The problem to be solved by the present invention is the biological production of 1,3-propanediol by a single organism from an inexpensive carbon substrate such as glucose or other sugars. The biological production of 1,3-propanediol requires glycerol as a substrate for a two step sequential reaction in which a dehydratase enzyme (typically a coenzyme $B_{12}$-dependent dehydratase) converts glycerol to an intermediate, 3-hydroxypropionaldehyde, which is then reduced to 1,3-propanediol by a NADH- (or NADPH) dependent oxidoreductase. The complexity of the cofactor requirements necessitates the use of a whole cell catalyst for an industrial process which utilizes this reaction sequence for the production of 1,3-propanediol. Furthermore, in order to make the process economically viable, a less expensive feedstock than glycerol or dihydroxyacetone is needed. Glucose and other carbohydrates are suitable substrates, but, as discussed above, are known to interfere with 1,3-propanediol production. As a result no single organism has been shown to convert glucose to 1,3-propanediol.

Applicants have solved the stated problem and the present invention provides for bioconverting a fermentable carbon source directly to 1,3-propanediol using a single organism. Glucose is used as a model substrate and the bioconversion is applicable to any existing microorganism. Microorganisms harboring the gene for a dehydratase are able to convert glucose and other sugars through the glycerol degradation pathway to 1,3-propanediol with good yields and selectivities. Furthermore, the present invention may be generally applied to include any carbon substrate that is readily converted to glycerol, dihydroxyacetone, or $C_3$ compounds at the oxidation state of glycerol (e.g., glycerol 3-phosphate) or dihydroxyacetone (e.g., dihydroxyacetone phosphate or glyceraldehyde 3-phosphate).

SUMMARY OF THE INVENTION

The present invention comprises a process for the bioconversion of a carbon substrate to 1,3-propanediol by a single microorganism having at least one gene capable of expressing a dehydratase enzyme by contacting said microorganism with said substrate. The microorganism can be a wild type, or genetically altered, such as a recombinant microorganism or a mutant of a microorganism. Preferably, the dehydratase enzyme is a glycerol dehydratase enzyme or a diol dehydratase enzyme.

The present invention further comprises the product of the above process.

The present invention further comprises a cosmid comprising a DNA fragment of about 35 kb isolated from *Klebsiella pneumoniae* wherein said fragment encodes an active glycerol dehydratase enzyme having the restriction digest in FIG. 1, columns 1 and 2. This cosmid, when transferred into a microorganism permits metabolism of a carbon substrate, in particular glucose, to 1,3-propanediol.

The present invention further comprises a transformed microorganism comprising a host microorganism and the above cosmid or any DNA fragment of said cosmid encoding an active functional protein other than a glycerol dehydratase enzyme.

BRIEF DESCRIPTION OF BIOLOGICAL DEPOSITS

Figure 1:
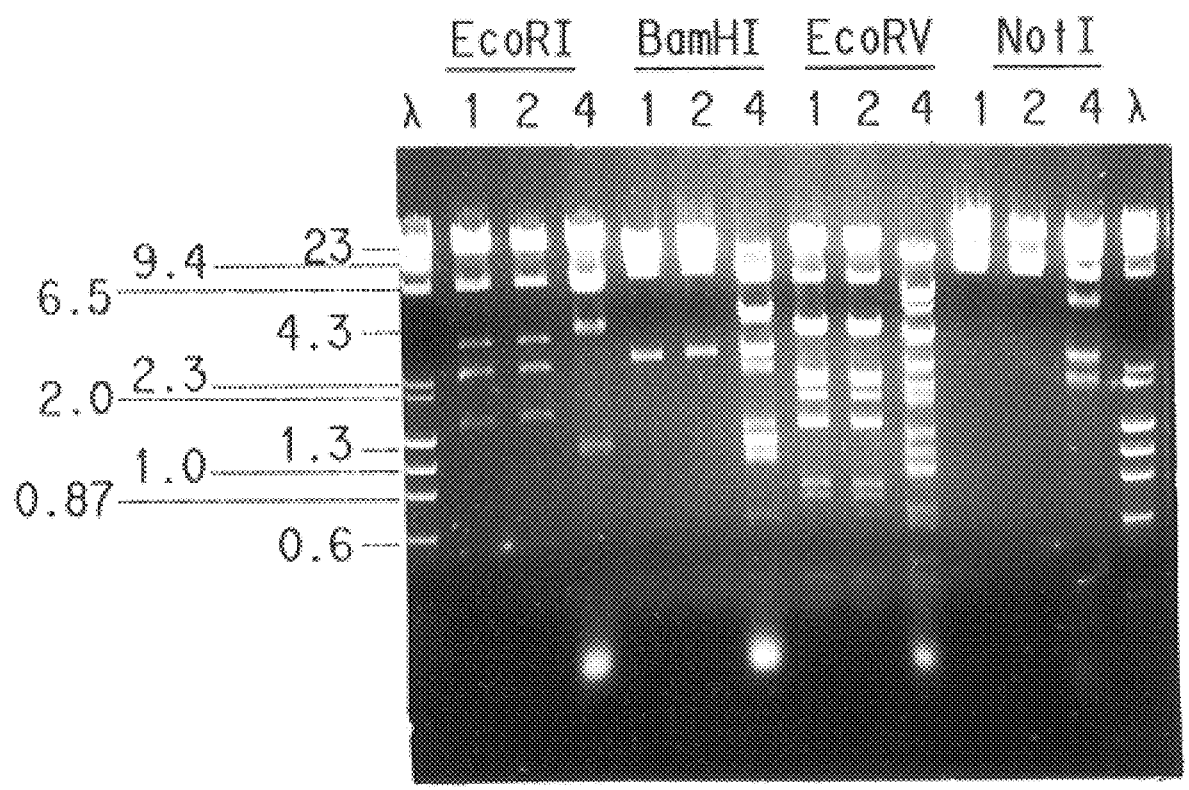
FIG. 1 shows restriction digests (EcoR 1, BamH 1, EcoR V and Not1) of cosmids pkP1, pKP2 and pKP4 labeled as columns 1, 2 and 4, respectively, and separation on a 0.8% agarose gel electrophoresis. Molecular size markers were loaded on the lanes in the end. Columns labeled as numbers 1 and 2 represent cosmids containing a glycerol dehydratase enzyme.
Figure 2:
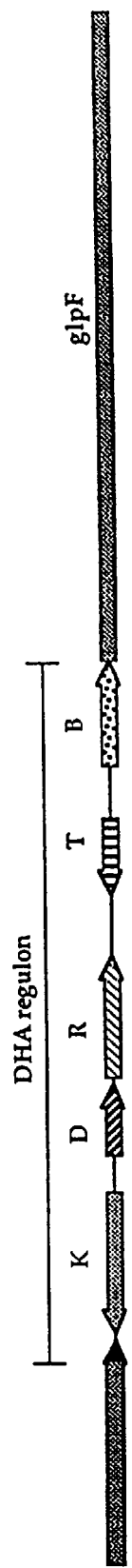
FIG. 2 shows a partial physical map of pKP1 and the position of the genes based on DNA sequence. The genes were identified based on comparison of deduced open reading frames with the Genbank data base using the Tfasta program provided by a sequence analysis software of the University of Wisconsin [Genetics Computer Group, Verison 7, April, 1991, 575 Science Drive, Madison, Wis. 53711].

The transformed *E. coli* DH5α containing cosmid pKP1 containing a portion of the *Klebsiella* genome encoding the glycerol dehydratase enzyme was deposited with the ATCC under the terms of the Budapest Treaty and is identified by the ATCC number ATCC 69789. The transformed *E. coli* DH5α containing cosmid pKP4 containing a portion of the *Klebsiella* genome encoding a diol dehydratase enzyme was deposited on Apr. 18, 1995 with the ATCC under the terms of the Budapest Treaty and is identified by the ATCC number ATCC 69790. "ATCC" refers to the American Type Culture Collection international depository located at 10801 University Blvd., Manassas, Va. 20110-2209, U.S.A.

DETAILED DESCRIPTION OF THE INVENTION

As used herein the following terms may be used for interpretation of the claims and specification.

The term "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "transformation" or "transfection" refers to the acquisition of new genes in a cell after the incorporation of nucleic acid. The term "transformant" refers to the product of a transformation. The term "genetically altered" refers to the process of changing hereditary material by transformation or mutation.

The term "expression" refers to the transcription and translation to gene product from a gene coding for the sequence of the gene product.

The term "plasmid" or "vector" or "cosmid" as used herein refers to an extra chromosomal element often carrying genes which are not part of the central metabolism of the cell, and usually in the form of circular double-stranded DNA molecules.

The term "dehydratase enzyme" will refer to any enzyme that is capable of isomerizing or converting a glycerol molecule to the product 3-hydroxypropion-aldehyde. For the purposes of the present invention the dehydratase enzymes include a glycerol dehydratase and a diol dehydratase having preferred substrates of glycerol and 1,2-propanediol, respectively.

The term "carbon substrate" or "carbon source" means any carbon source capable of being metabolized by a microorganism wherein the substrate contains at least one carbon atom, provided that the carbon substrate is other than glycerol or dihydroxyacetone.

The term "ATCC" will stand for the American Type Culture Collection, 10801 University Blvd., Manassas, Va. 20110-2209, U.S.A.

The present invention provides a method for a biological production of 1,3-propanediol from a fermentable carbon source in a single organism. The method incorporates a microorganism containing a dehydratase enzyme which is contacted with a carbon substrate and 1,3-propanediol is isolated from the growth media. The single organism may be a wild type organism or may be a genetically altered organism harboring a gene encoding a dehydratase enzyme.

The present method provides a rapid, inexpensive and environmentally responsible source of 1,3-propanediol monomer useful in the production of polyesters and other polymers.

Construction of Recombinant Organisms

Recombinant organisms containing the necessary genes that will encode the enzymatic pathway for the conversion of a carbon substrate to 1,3-propanediol may be constructed using techniques well known in the art. In the present invention genes encoding dehydratase enzyme were isolated from a native host such as *Klebsiella* and used to transform the *E. coli* host strains DH5α, ECL707 and AA200.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (U.S. Pat. No. 4,683,202) to obtain amounts of DNA suitable for transformation using appropriate vectors.

Alternatively, cosmid libraries may be created where large segments of genomic DNA (35–45kb) may be packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook, J. et al., *Molecular Cloning: A Laboratory Manual*, Second Edition (1989) Cold Spring Harbor Laboratory Press, herein incorporated by reference.

Typically to clone cosmids, foreign DNA is isolated and ligated, using the appropriate restriction endonucleases, adjacent to the cos region of the cosmid vector. Cosmid vectors containing the linearized foreign DNA is then reacted with a DNA packaging vehicle such as bacteriophage λ. During the packaging process the cos sites are cleaved and the foreign DNA is packaged into the head portion of the bacterial viral particle. These particles are then used to transfect suitable host cells such as *E. coli*. Once injected into the cell, the foreign DNA circularizes under the influence of the cos sticky ends. In this manner large segments of foreign DNA can be introduced and expressed in recombinant host cells.

Cosmid vectors and cosmid transformation methods were used within the context of the present invention to clone large segments of genomic DNA from bacterial genera known to possess genes capable of processing glycerol to 1,3-propanediol. Specifically, genomic DNA from *K. pneumoniae* was isolated by methods well known in the art and digested with the restriction enzyme Sau3A for insertion into a cosmid vector Supercos 1™ and packaged using GigapackII™ packaging extracts. Following construction of the vector *E. coli* XL1-Blue MR cells were transformed with the cosmid DNA. Transformants were screened for the ability to convert glycerol to 1,3-propanediol by growing the cells in the presence of glycerol and analyzing the media for 1,3-propanediol formation.

Two of the 1,3-propanediol positive transformants were analyzed and the cosmids were named pKP1 and pKP2. DNA sequencing revealed extensive homology to the glycerol dehydratase gene from *C. freundii*, demonstrating that these transformants contained DNA encoding the glycerol dehydratase gene. Other 1,3-propanediol positive transformant were analyzed and the cosmids were named pKP4 and pKP5. DNA sequencing revealed that these cosmids carried DNA encoding a diol dehydratase gene.

Although the instant invention utilizes the isolated genes from within a *Klebsiella* cosmid, alternate sources of dehydratase genes include, but are not limited to, *Citrobacter, Clostridia,* and *Salmonella.*

Other genes that will positively affect the production of 1,3-propanediol may be expressed in suitable hosts. For example it may be highly desirable to over-express certain enzymes in the glycerol degradation pathway and/or other pathways at levels far higher than currently found in wild type cells. This may be accomplished by the selective cloning of the genes encoding those enzymes into multicopy plasmids or placing those genes under a strong inducible or constitutive promoter. Methods for over-expressing desired proteins are common and well known in the art of molecular biology and examples may be found in Sambrook, supra. Furthermore, specific deletion of certain genes by methods known to those skilled in the art will positively affect the production of 1,3-propanediol. Examples of such methods can be found in *Methods in Enzymology*, Volume 217, R. Wu editor, Academic Press:San Diego 1993.

Mutants

In addition to the cells exemplified it is contemplated that the present method will be able to make use of cells having single or multiple mutations specifically designed to enhance the production of 1,3-propanediol. Cells that normally divert a carbon feed stock into non-productive pathways, or that exhibit significant catabolite repression could be mutated to avoid these phenotypic deficiencies. For example, many wild type cells are subject to catabolite repression from glucose and by-products in the media and it is contemplated that mutant strains of these wild type organisms, capable of 1,3-propanediol production that are resistant to glucose repression, would be particularly useful in the present invention.

Methods of creating mutants are common and well known in the art. For example, wild type cells may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible but are generally not as effective as the short wave UV light unless used in conjunction with various activators such as psoralen dyes that interact with the DNA.

Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See Brock, Supra., DeMancilha et al., *Food Chem.*, 14, 313, (1984).

Mutations and transformations in the 1,3-propanediol production pathway

Representative enzyme pathway. The production of 1,3-propanediol from glucose can be accomplished by the following series of steps. This series is representative of a number of pathways known to those skilled in the art. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or reduction of DHAP to glycerol 3-phosphate (G3P) followed by hydrolysis. The hydrolysis step can be catalyzed by any number of cellular phosphatases which are known to be non-specific with respect to their substrates or the activity can be introduced into the host by recombination. The reduction step can be catalyzed by a $NAD^+$(or $NADP^+$) linked host enzyme or the activity can be introduced into the host by recombination. It is notable that the dha regulon contains a glycerol dehydrogenase (E.C. 1.1.1.6) which catalyzes the reversible reaction of Equation 3.

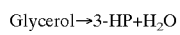 (Equation 1)

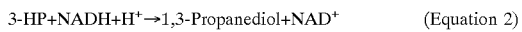 (Equation 2)

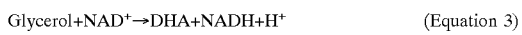 (Equation 3)

Glycerol is converted to 1,3-propanediol via the intermediate 3-hydroxypropionaldehye (3-HP) as has been described in detail above. The intermediate 3-HP is produced from glycerol, Equation 1, by a dehydratase enzyme which can be encoded by the host or can introduced into the host by recombination. This dehydratase can be glycerol dehydratase (E.C. 4.2.1.30), diol dehydratase (E.C. 4.2.1.28) or any other enzyme able to catalyze this transformation. Glycerol dehydratase, but not diol dehydratase, is encoded by the dha regulon. 1,3-Propanediol is produced from 3-HP, Equation 2, by a $NAD^+$- (or $NADP^+$) linked host enzyme or the activity can introduced into the host by recombination. This final reaction in the production of 1,3-propanediol can be catalyzed by 1,3-propanediol dehydrogenase (E.C. 1.1.1.202) or other alcohol dehydrogenases.

Mutations and tranformations that affect carbon channeling. A variety of mutant organisms comprising variations in the 1,3-propanediol production pathway will be useful in the present invention. For example the introduction of a triosephosphate isomerase mutation (tpi-) into the microorganism of the present invention is an example of the use of a mutation to improve the performance by carbon channeling. The mutation can be directed toward a structural gene so as to impair or improve the activity of an enzymatic activity or can be directed toward a regulatory gene so as to modulate the expression level of an enzymatic activity.

Alternatively, transformations and mutations can be combined so as to control particular enzyme activities for the enhancement of 1,3-propanediol production. Thus it is within the scope of the present invention to anticipate modifications of a whole cell catalyst which lead to an increased production of 1,3-propanediol.

Media and Carbon Substrates

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. Glycerol production from single carbon sources (e.g., methanol, formaldehyde or formate) has been reported in methylotrophic yeasts (K. Yamada et al. *Agric. Biol. Chem.* 53(2) 541–543, (1989)) and in bacteria (Hunter et.al., *Biochemistry*, 24, 4148–4155, (1985)). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York (1986)). The ribulose monophosphate pathway involves the condensation of formate with ribulose-5-phosphate to form a 6 carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth C1 Compd., [Int. Symp..], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* (1990), 153(5), 485–9). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention preferred are glucose, fructose, sucrose or methanol.

In addition to an appropriate carbon source, fermentation media must contain suitable minerals, salts, cofactors, buffers and other components, known to those skilled in the art, suitable for the growth of the cultures and promotion of the enzymatic pathway necessary for 1,3-propanediol production. Particular attention is given to Co(II) salts and/or vitamin $B_{12}$ or precursors thereof.

Culture Conditions

Typically cells are grown at 30° C. in appropriate media. Preferred growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate, may also be incorporated into the reaction media.

Suitable pH ranges for the fermentation are between pH 5.0 to pH 9.0 where pH 6.0 to pH 8.0 is preferred as the initial condition.

Reactions may be performed under aerobic or anaerobic conditions where anaerobic or microaerobic conditions are preferred.

Batch and Continuous Fermentations

The present process employs a batch method of fermentation. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1,3-propanediol production.

Identification and Purification of 1.3-propanediol

Methods for the purification of 1,3-propanediol from fermentation media are known in the art. For example propanediols can be obtained from cell media by subjecting the reaction mixture to extraction with an organic solvent, distillation and column chromatography (U.S. Pat. No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. Preferred in the present invention is a method where fermentation media is analyzed on an analytical ion exchange column using a mobile phase of 0.01N sulfuric acid in an isocratic fashion.

Cells

Cells suitable in the present invention comprise those that harbor a dehydratase enzyme. Typically the enzyme will be either a glycerol dehydratase or a diol dehydratase having a substrate specificity for either glycerol or 1,2-propanediol, respectively. Dehydratase enzymes are capable of converting glycerol to hydroxypropionaldehyde (3-HPA) which is then converted to 1,3-propanediol. Cells containing this pathway may include mutated or recombinant organisms belonging to the genera *Citrobacter, Enterobacter, Clostridium, Klebsiella, Samonella,* and *Lactobacillus*. Microorganisms known by persons skilled in the art to produce glycerol by fermentation, e.g., *Aspergillus,*

Saccharomyces, Zygosaccharomyces, Pichia, Kluyveromyces, Candida, Hansenula, Dunaliella, Debaryomyces, Mucor, Torylopsis, and Methylobacteria, may be the hosts for a recombinant dehydratase enzyme. Other cells suitable as hosts in the present invention include Bacillus and Escherichia. While not wishing to be bound by theory, it is believed that organisms, belonging to the above mentioned groups, exist in nature that are suitable for the present invention.

On the basis of applicants' experimental work it is contemplated that a wide variety of cells may be used in the present invention. Applicants have demonstrated for example that cells varying widely in genetic and phenotypic composition are able to bioconvert a suitable carbon substrate to 1,3-propanediol. Cells exemplified include: a K. pneumoniae mutant strain constitutive for the dha genes, recombinant E. coli strains comprising elements of the Klebsiella genome containing genes encoding either glycerol or diol dehydratase, and recombinant E. coli (tpi$^-$) strains also transfected with elements of the Klebsiella genomes and harboring a mutation in the gene encoding the triosephosphate isomerase enzyme.

Although E. coli transformants containing the dba regulon from Klebsiella pneumonia were able to convert glycerol to 1,3-propanediol even in the presence of glucose or xylose (Tong et al., Appl. Biochem. Biotech., 34, 149 (1992)) no 1,3-propanediol was detected by these organisms in the presence of glucose alone. In direct contrast to this disclosure, applicants have discovered that three strains of E. coli, containing either of two independently isolated cosmids comprising the dha regulon from Klebsiella pneumonia, produced 1,3-propanediol from a feed of glucose with no exogenously added glycerol present. E. coli strain ECL707, containing cosmid vectors pKP-1 or pKP-2 comprising the K. pneumoniae dha regulon, showed detectable though modest production of 1,3-propanediol from glucose in the absense of exogenously added glycerol, (Example 3). Recombinant E. coli strains constructed from an alternate host organism, DH5α, also containing cosmid vectors pKP-1 or pKP-2, were found to be more effective than the ECL707 recombinants in producing 1,3-propanediol from glucose under the appropriate conditions, (Example 2). Most effective in producing 1,3-propanediol from glucose under the conditions of Example 3 were the recombinant E. coli strains AA200 containing cosmid vectors pKP-1 or pKP-2, Example 1. E. coli strain AA200 contains a defective triosephosphate isomerase enzyme (tpi$^-$).

A strain of AA200-pKP1, selected for further study from a pool of independent isolates from the transformation reaction, converted glucose to 1,3-propanediol in a two stage reaction. In the first stage, the strain AA200-pKP1–5 was grown to high cell density in the absence of glucose and glycerol. In the second stage, the grown cells, suspended in a medium containing glucose but no glycerol, converted glucose to 1,3-propanediol with high conversion and selectivity, Example 4. Although differing immumochemically, chromatographically, and genetically, the coenzyme $B_{12}$-dependent enzymes glycerol dehydratase (E.C. 4.2.1.30) and diol dehydratase (E.C. 4.2.1.28) catalyze the conversion of glycerol to 3-hydroxypropionaldehyde. Glycerol dehydratase, but not diol dehydratase, is encompassed by the dha regulon. K. pneumoniae ATCC 8724, containing a diol dehydratase but not a glycerol dehydratase converts glycerol to 1,3-propanediol (Forage et al., J. Bacteriol., 149, 413, (1982)). Recombinant E. coli strains ECL707 and AA200, containing cosmid vector pKP4 encoding genes for a diol dehydratase, converted glucose to 1,3-propanediol, Example 1 and Example 3.

K. pneumoniae ECL2106, prepared by mutagenesis from a naturally occurring strain (Ruch et al., J. Bacteriol. 124, 348 (1975)), exibits constitutive expression of the dha regulon (Ruch et al., supra; Johnson et al., J. Bacteriol. 164, 479 (1985)). A strain derived from K. pneumoniae ATCC 25955, displaying the same phenotype, has been similarly prepared (Forage et al., J. Bacteriol. 149, 413 (1982)). Expression of the Klebsiella dha structural genes is, in part, controlled by a repressor (product of dha R) (Sprenger et al., J. Gen Microbiol. 135, 1255 (1989)). Applicants have shown that ECL2106, which is constitutive for the dha structural genes, produced 1,3-propanediol from a feed of glucose in the absence of exogenously added glycerol, Example 5. This is in contrast to wild type K. pneumoniae ATCC 25955 which did not produce detectable levels of 1,3-propanediol under the same conditions, Example 5.

The expression of the dha structural genes in ECL2106 is further controlled by catabolite expression (Sprenger et al., J. Gen Microbiol. 135, 1255 (1989)). Elimination of catabolite repression can be achieved by placing the necessary structural genes under the control of alternate promoters as has been demonstrated for 1,3-propanediol oxidoreductase (dhaT) from C. freundii and diol dehydratase from K. oxytoca ATCC 8724 (Daniel et al., J. Bacterial. 177, 2151 (1995) and Tobimatsu et al., J. Biol. Chem. 270, 7142 (1995)). By eliminating catabolite repression from ECL2106 in this manner, an improvement in the production of 1,3-propanediol from glucose in the absence of an exogenous source of glycerol is achieved. An even further improvement is obtained by appropriate carbon channelling as is described, by example, with the tpi$^-$mutation.

As the dha regulons of Citrobacter and Klebsiella sp. are strikingly similar, one of skill in the art will appreciate that teachings that involve the production of 1,3-propanediol from glucose in the absence of an exogenous source of glycerol for Klebsiella sp. applies to Citrobacter sp. as well. Furthermore, as the metabolism of glycerol by C. butyricum is comparable to that of K. pneumoniae [Zeng et al., Biotechnol. and Bioeng. 44, 902 (1994)], teachings will extend to Clostridia sp. as well.

EXAMPLES

GENERAL METHODS

Restriction enzyme digestions, phosphorylations, ligations and transformations were done as described in Sambrook, J. et al., Molecular Cloning: A Laboratory Manual, Second Edition, Cold Spring Harbor Laboratory Press (1989).

Materials and methods suitable for the maintenance and growth of bacterial cultures were found in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), pp. 210–213, American Society for Microbiology, Washington, D.C. or Thomas D. Brock in Biotechnology: A Textbook of Industrial Microbiology, Second Edition (1989) Sinauer Associates, Inc., Sunderland, Mass. All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mis.) unless otherwise specified.

The meaning of abbreviations is as follows: "h" means hour(s), "min" means minute(s), "sec" means second(s), "d" means day(s), "mL" means milliliters, "L" means liters, 50 amp is 50 μg/ml ampicillin, and LB-50 amp is Luria-Bertani broth containing 50 μg/ml ampicillin.

Within the tables the following abreviations are used. "Con." is conversion, "Sel." is selectivity, and "nd" is not detected.

Media

Synthetic S12 medium was used in the screening of bacterial transformants for the ability to make 1,3-propanediol. S12 medium contains: 10 mM ammonium sulfate, 50 mM potassium phosphate buffer, pH 7.0, 2 mM $MgCl_2$, 0.7 mM $CaCl_2$, 50 $\mu$M $MnCl_2$, 1 $\mu$M $FeCl_3$, 1 $\mu$M ZnCl, 1.7 $\mu$M $CuSO_4$, 2.5 $\mu$M $CoCl_2$, 2.4 $\mu$M $Na_2MoO_4$, and 2 $\mu$M thiamine hydrochloride.

Medium A used for growth and fermentation consisted of: 10 mM ammonium sulfate; 50 mM MOPS/KOH buffer, pH 7.5; 5 mM potassium phosphate buffer, pH 7.5; 2 mM $MgCl_2$; 0.7 mM $CaCl_2$; 50 $\mu$M $MnCl_2$; 1 $\mu$M $FeCl_3$; 1 $\mu$M ZnCl; 1.72 $\mu$M $CuSO_4$; 2.53 $\mu$M $CoCl_2$; 2.42 $\mu$M $Na_2MoO_4$; 2 $\mu$M thiamine hydrochloride; 0.01% yeast extract; 0.01% casamino acids; 0.8 $\mu$g/mL vitamin $B_{12}$; and 50 amp. Medium A was supplemented with either 0.2% glycerol or 0.2% glycerol plus 0.2% D-glucose as required.

Cells

*Klebsiella pneumoniae* ECL2106 (Ruch et al., *J. Bacteriol.*, 124, 348 (1975)), also known in the literature as *K. aerogenes* or *Aerobacter aerogenes*, was obtained from E. C. C. Lin (Harvard Medical School, Cambridge, Mass.) and was maintained as a laboratory culture.

*Klebsiella pneumoniae* ATCC 25955 was purchased from American Type Culture Collection (Manassas, Va.).

*E. coli* DH5α was purchased from Gibco/BRL and was transformed with the cosmid DNA isolated from *Klebsiella pneumoniae* ATCC 25955 containing a gene coding for either a glycerol or diol dehydratase enzyme. Cosmids containing the glycerol dehydratase were identified as pKP1 and pKP2 and cosmid containing the diol dehydratase enzyme were identified as pKP4. Transformed DH5α cells were identified as DH5α-pKP1, DH5α-pKP2, and DH5α-pKP4.

*E. coli* ECL707 (Sprenger et al., *J. Gen. Microbiol.* 135, 1255 (1989)) was obtained from E. C. C. Lin (Harvard Medical School, Cambridge, Mass.) and was similarly transformed with cosmid DNA from *Klebsiella pneumoniae*. These transformants were identified as ECL707-pKP1 and ECL707-pKP2, containing the glycerol dehydratase gene and ECL707-pKP4 containing the diol dehydratase gene.

*E. coli* AA200 containing a mutation in the tpi gene (Anderson et al., *J. Gen Microbiol.*, 62, 329 (1970)) was purchased from the *E. coli* Genetic Stock Center, Yale University (New Haven, Conn.) and was transformed with *Klebsiella* cosmid DNA to give the recombinant organisms AA200-pKP1 and AA200-pKP2, containing the glycerol dehydratase gene, and AA200-pKP4, containing the diol dehydratase gene.

Isolation and Identification 1,3-propanediol

The conversion of glycerol to 1,3-propanediol was monitored by HPLC. Analyses were performed using a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01N $H_2SO_4$ as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of 1,3-propanediol was confirmed by GC/MS with a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated from glycerol were compared to that of authentic 1,3-propanediol (m/e: 57, 58).

Construction of *K. pneumonlae* cosmid libraries

*K. pneumoniae* (ATCC 25955) was grown in 100 ml LB medium for 8 h at 37° C. with aeration. Bacteria (25 ml per tube) were centrifuged at 3,000 rpm for 15 min in a DuPont Sorvall GLC 2.B centrifuge at room temperature. The bacteria were pelleted and supernatant was decanted. The bacterial cell pellet was frozen at −20° C. The chromosomal DNA was isolated as outlined below with special care taken to avoid shearing of DNA (i.e., vortexing was avoided). One tube of bacteria was resuspended in 2.5 ml of 50 mM Tris-10 mM EDTA and 500 $\mu$l of lysozyme (1 mg/ml) was added. The pellet was gently resuspended and the suspension was incubated at 37° C. for 15 min. Sodium dodecyl sulfate was added to bring the final concentration to 0.5%. This resulted in the solution becoming clear. Proteinase K (50 ug/ml) was added and the suspension was incubated at 55° C. for 2 h. The tube was removed and transferred to an ice bath and sodium chloride was added to yield a 0.4M final concentration. Two volumes of ethanol were added to the liquid. A glass tube was inserted to the interface and the DNA was gently spooled. DNA was dipped into a tube containing 70% ethanol. After drying in vacuo, the DNA was resuspended in 500 ul of water and the concentration of DNA was determined spectrophotometrically. A diluted aliquot of DNA was run on a 0.5% agarose gel to determine the intact nature of DNA.

The chromosomal DNA was partially digested with Sau3A as outlined by Sambrook et al., supra. DNA (2 ug) was digested with 2 units of Sau3A (Promega, Madison, Wis.) at room temperature in 200 $\mu$l of total volume. At 0, 5, 10 and 20 min, samples (50 $\mu$l) were removed and transferred to tubes containing 5 umol of EDTA. These tubes were incubated at 70° C. for 10 min. An aliquot (2 $\mu$l) was withdrawn and analyzed on a 0.5% agarose gel electrophoresis to determine the level of digestion and the rest of the sample (48 $\mu$l) was stored at −20° C. The gel was stained with ethidium bromide and visualized under UV to determine the partial digestion of the chromosomal DNA. A decrease in the size of the chromosomal DNA with increase in time was observed showing that the decrease in the size of the chromosomal DNA is due to the action of Sau3A. DNA was extracted from rest of the sample by standard protocol methods (Sambrook et al., supra).

A cosmid library of partially digested DNA from *K. pneumoniae* was prepared using Supercos™ cosmid vector kit and GigapackII™ packaging extracts using reagents purchased from Stratagene (La Jolla, Calif.). The instructions provided by the manufacturer were followed. The packaged *K. pneumoniae* contained $4×10^4$ to $1.0×10^5$ phage titer as determined by transfecting *E. coli* XL1-Blue MR.

Cosmid DNA was isolated from 6 of the *E. coli* transformants and found to contain large insert of DNA (25 to 30 kb).

Transformation of Host Cells with cosmid DNA: DH5α

Six transformation plates containing approximately 1,000 colonies of *E. coli* XL1-Blue MR transfected with *K. pneumoniae* DNA were washed with 5 ml LB medium and centrifuged. The bacteria were pelleted and resuspended in 5 ml LB medium+glycerol. An aliquot (50 $\mu$l) was inoculated into a 15 ml tube containing S12 synthetic medium with 0.2% glycerol+400 ng per ml of vitamin $B_{12}$+0.001% yeast extract +50 amp. The tube was filled with the medium to the top and wrapped with parafilm and incubated at 30° C. A slight turbidity was observed after 48 h. Aliquots, analyzed for product distribution as described above at 78 h and 132 h, were positive for 1,3-propanediol, the later time points containing increased amounts of 1,3-propanediol.

The bacteria, testing positive for 1,3-propanediol production, were serially diluted and plated onto LB-50 amp plates in order to isolate single colonies. Forty eight single colonies were isolated and checked again for the production of 1,3-propanediol. Cosmid DNA was isolated from 6 independent clones and transformed into *E. coli* strain DH5α. The transformants were again checked for the production of 1,3-propanediol. Cells testing positive for 1,3-propanediol production were designated: DH5α-pKP1, DH5α-pKP2, and DH5α-pKP4.

ECL707

*E. coli* strain ECL707 was transformed with cosmid *K. pneumoniae* DNA corresponding to pKP1, pKP2, pKP4 and the Supercos™ vector alone and was named ECL707-pKP1, ECL707-pKP2, ECL707-pKP4, and ECL707-sc, respectively. ECL707 is defective in glpK, gld, and ptsD which encode the ATP-dependent glycerol kinase, NAD+-linked glycerol dehydrogenase, and enzyme II for dihydroxyacetone of the phosphoenolpyruvate dependent phosphotransferase system, respectively.

Twenty single colonies of each cosmid transformation and five of the Supercos vector alone (negative control) transformation, isolated from LB-50 amp plates, were transferred to a master LB-50 amp plate. These isolates were also tested for their ability to convert glycerol to 1,3-propanediol in order to determine if they contained dehydratase activity. The transformants were transferred with a sterile toothpick to microtiter plates containing 200 μL of Medium A supplemented with either 0.2% glycerol or 0.2% glycerol plus 0.2% D-glucose. After incubation for 48 hr at 30° C, the contents of the microtiter plate wells were filtered through an 0.45μ nylon filter and chromatographed by HPLC. The results of these tests are given in Table 1.

TABLE 1

Conversion of glycerol to 1,3-propanediol by transformed ECL707: number of positive isolates/number of isolates tested

| Transformant | Glycerol | Glycerol plus Glucose |
|---|---|---|
| ECL707-pKP1 | 19/20 | 19/20 |
| ECL707-pKP2 | 18/20 | 20/20 |
| ECL707-PkP4 | 0/20 | 20/20 |
| ECL707-sc | 0/5 | 0/5 |

AA200

*E. coli* strain AA200 was transformed with cosmid *K. pneumoniae* DNA corresponding to pKP1, pKP2, pKP4 and the Supercos™ vector alone and was named AA200-pKP1, AA200-pKP2, AA200-pKP4, and AA200-sc, respectively. Strain AA200 is defective in triosephosphate isomerase, (tpi−)

Twenty single colonies of each cosmid transformation and five of the empty vector transformation were isolated and tested for their ability to convert glycerol to 1,3-propanediol as described for *E. coli* strain ECL707. The results of these tests are given in Table 2.

TABLE 2

Conversion of glycerol to 1,3-propanediol by transformed AA200: Number of positive isolates/number of isolates tested

| Transformant | Glycerol | Glycerol plus Glucose |
|---|---|---|
| AA200-pKP1 | 17/20 | 17/20 |
| AA200-pKP2 | 17/20 | 17/20 |
| AA200-pKP4 | 2/20 | 16/20 |
| AA200-sc | 0/5 | 0/5 |

EXAMPLE 1

Conversion of D-glucose to 1,3-propanediol by *E. coli* strain AA200, transformed with *Klebsiellia pneumoniae* DNA containing dehydratase activity Glass serum bottles, filled to capacity with media (ca. 14 mL of Medium A supplemented with 10 μg/mL kanamycin and 0.2% D-glucose, plus or minus 0.5–1.0 mM cyclic adenosine 2':3'-monophosphate (cAMP)), were innoculated with selected single colony isolates of *E. coli* strain AA200 containing the *K. pneumoniae dha* regulon cosmids pKP1 or pKP2, the *K. pneumoniae pdu* operon pKP4, or the Supercos™ vector alone. In order to avoid contact with glycerol, the innoculation was performed from either an agar plate of LB-50 amp or from a liquid culture of the same medium. The reactions were incubated for ca. 72 hr at 30° C. while shaking at 250 rpm. Growth was determined by the change in absorbance at 600 nm where the initial $OD_{600}$ was ≦0.020 AU. The extent of glucose depletion and product 20 distribution were determined by HPLC. Single colony isolates are identified by a numbered suffix "-x", e.g. AA200-pKP1-x. Cumulative results are presented in Table 3 and Table 4.

TABLE 3

Conversion of 0.2% D-glucose to 1,3-propanediol by transformed *E. coli* strain AA200: without cAMP

| Transformant | $OD_{600}$ | [1,3-propane-diol] (mM) | Con. (%) | Sel. (%) |
|---|---|---|---|---|
| AA200-pKP1-3 | 0.056 | 0.05 | 17 | 1 |
| AA200-pKP1-5 | 0.115 | nd | 0 | |
| " | 0.007 | nd | 0 | |
| " | 0.076 | 0.2 | 14 | 5 |
| AA200-pKP1-20 | 0.116 | nd | 27 | 0 |
| " | 0.205 | 0.3 | 17 | 8 |
| AA200-pKP2-10 | 0.098 | 0.2 | 13 | 7 |
| AA200-pKP2-14 | 0.117 | 0.5 | 17 | 14 |
| " | 0.129 | 0.2 | 19 | 5 |
| AA200-pKP2-20 | 0.094 | nd | 11 | 0 |
| AA200-pKP4-4 | 0.198 | 0.1 | 28 | 2 |
| AA200-pKP4-19 | 0.197 | 0.2 | 34 | 3 |
| AA200-pKP4-20 | 0.206 | 0.1 | 38 | 1 |
| AA200-sc-1 | 0.097 | nd | 22 | 0 |
| " | 0.176 | nd | 46 | 0 |

TABLE 4

Conversion of 0.2% D-glucose to 1,3-propanediol by transformed *E. coli* strain AA200: with cAMP

| Transformant | $OD_{600}$ | [1,3-propane-diol] (mM) | % Con. | % Sel. |
|---|---|---|---|---|
| AA200-pKP1-3 | 0.102 | 0.5 | 19 | 12 |
| AA200-pKP1-5 | 0.088 | 1.5 | 21 | 37 |

TABLE 4-continued

Conversion of 0.2% D-glucose to 1,3-propanediol by
transformed *E. coli* strain AA200: with cAMP

| Transformant | OD$_{600}$ | [1,3-propane-diol] (mM) | % Con. | % Sel. |
|---|---|---|---|---|
| " | 0.236 | 1.4 | 24 | 28 |
| " | 0.071 | 0.8 | 15 | 23 |
| AA200-pKP1-20 | 0.153 | nd | 40 | 0 |
| " | 0.185 | 0.9 | 27 | 16 |
| AA200-pKP2-10 | 0.098 | 0.2 | 13 | 7 |
| AA200-pKP2-14 | 0.213 | 2.0 | 26 | 27 |
| " | 0.155 | 0.6 | 25 | 12 |
| AA200-pKP2-20 | 0.198 | 1.2 | 40 | 14 |
| AA200-pKP4-4 | 0.218 | 0.1 | 31 | 2 |
| AA200-pKP4-19 | 0.223 | 0.2 | 37 | 3 |
| AA200-pKP4-20 | 0.221 | 0.2 | 35 | 3 |
| AA200-sc-1 | 0.111 | nd | 23 | 0 |
| " | 0.199 | nd | 49 | 0 |
| " | 0.122 | nd | 25 | 0 |

EXAMPLE 2

Conversion of D-glucose to 1,3-propanediol by *E. coli* strain DH5α, transformed with *Klebsiellia pneumoniae* DNA containing dehydratase activity

*E. coli* strain DH5α, containing the *K. pneumoniae dha* regulon cosmids pKP1 or pKP2, were tested for their ability to convert D-glucose to 1,3-propanediol exactly as described in Example 1. The results are presented in Table 5.

TABLE 5

Conversion of 0.2% D-glucose to 1,3-propanediol by transformed
*E. coli* strain DH5α: plus (+) and minus (−) cAMP

| Transformant | OD$_{600}$ | [1,3-propane-diol] (mM) | % Con. | % Sel. |
|---|---|---|---|---|
| DH5α-pKP1 (−) | 0.630 | 0.5 | 100 | 2 |
| DH5α-pKP1 (+) | 0.774 | 0.6 | 100 | 3 |
| DH5α-pKP2 (−) | 0.584 | 0.6 | 100 | 3 |
| DH5α-pKP2 (+) | 0.699 | 0.7 | 100 | 3 |

EXAMPLE 3

Conversion of D-glucose to 1,3-propanediol by *E. coli* strain ECL707, transformed with *Klebsiellia pneumoniae* DNA containing dehydratase activity

*E. coli* strain ECL707, containing the *K. pneumoniae dha* regulon cosmids pKP1 or pKP2, the *K. pneumoniae pdu* operon pKP4, or the Supercos™ vector alone, were tested for their ability to convert D-glucose to 1,3-propanediol exactly as described in Example 1. In each case, conversion was quantitative. The results are presented in Table 6.

TABLE 6

Conversion of D-glucose to 1,3-propanediol by transformed
*E. coli* strain ECL707: with and without cAMP

| Transformant | OD$_{600}$ (without cAMP) | [1,3-propane-diol] (mM) (without cAMP) | OD$_{600}$ (with cAMP) | [1,3-propane-diol] (mM) (with cAMP) |
|---|---|---|---|---|
| ECL707-pKP1-1 | 0.607 | 0.1 | 0.475 | 0.1 |
| ECL707-pKP1-3 | 0.619 | 0.1 | 0.422 | 0.1 |
| ECL707-pKP1-7 | 0.582 | 0.2 | 0.522 | 0.2 |

TABLE 6-continued

Conversion of D-glucose to 1,3-propanediol by transformed
*E. coli* strain ECL707: with and without cAMP

| Transformant | OD$_{600}$ (without cAMP) | [1,3-propane-diol] (mM) (without cAMP) | OD$_{600}$ (with cAMP) | [1,3-propane-diol] (mM) (with cAMP) |
|---|---|---|---|---|
| ECL707-pKP1-10 | 0.593 | 0.1 | 0.408 | 0.1 |
| ECL707-pKP1-18 | 0.584 | 0.1 | 0.433 | 0.1 |
| ECL707-pKP2-4 | 0.588 | 0.1 | 0.408 | 0.1 |
| ECL707-pKP2-5 | 0.630 | 0.1 | 0.516 | 0.2 |
| ECL707-pKP2-8 | 0.542 | 0.1 | 0.486 | 0.1 |
| ECL707-pKP2-15 | 0.589 | 0.1 | 0.485 | 0.1 |
| ECL707-pKP2-19 | 0.577 | 0.1 | 0.504 | 0.1 |
| ECL707-pKP4-8 | 0.499 | nd | 0.361 | <0.1 |
| ECL707-pKP4-9 | 0.544 | nd | 0.354 | nd |
| ECL707-pKP4-10 | 0.515 | nd | 0.265 | <0.1 |
| ECL707-pKP4-14 | 0.512 | nd | 0.318 | <0.1 |
| ECL707-pKP4-17 | 0.545 | nd | 0.388 | <0.1 |
| ECL707-sc-1 | 0.592 | nd | 0.385 | nd |

EXAMPLE 4

Two stage conversion of D-glucose to 1,3-propanediol by *Escherichia coli* AA200-pKP1–5

Baffled flasks (250 mL) containing 50 mL LB-amp medium were inoculated with single colonies of AA200-pKP1–5. The cells were grown, in duplicate, overnight at 30 or 37° C. with shaking (250 rpm).

Grown cultures were spun (10 minutes, 10,000 rpm, 4° C.) and resuspended in production medium without glucose (10 mM (NH$_4$)$_2$SO$_4$; 5 mM potassium phosphate buffer, pH 7.5; 50 mM MOPS, pH 7.5; 0.01% yeast extract; 0.01% casamino acids; 0.8 μg/mL vitamin B12; and 50 μg/mL ampicillin) containing either trace metals A: (0.08 μM CoCl$_2$, 0.06 μM CuCl$_2$, 7 μM FeSO$_4$, 2 μM H$_3$BO$_4$, 0.2 μM MnCl$_2$, 0.1 μM Na$_2$MoO$_4$, 0.08 μM NiCl$_2$, 0.3 μM ZnSO$_4$, and 0.03 mM thiamine) or trace metals B: (0.7 mM CaCl$_2$, 2.53 μM CoCl$_2$, 1.72 μM CuSO$_4$, 1.0 μM FeCl$_3$, 2 mM MgCl$_2$, 0.05 mM MnCl$_2$, 2.42 μM Na$_2$MoO$_4$, 1.0 μM ZnCl$_2$, and 0.03 mM thiamine). The cells were spun a second time, resuspended in 50 ml fresh production medium containing D-glucose and dispensed into 60 mL serum bottles which were capped and sealed with butyl rubber septa. The bottles were shaken (250 rpm) and samples withdrawn with a syringe through the septum and filtered through a 0.2μ0 filter before analysis. Results are shown in Table 7 and Table 8; residual glucose was measured by enzymatic analysis (Biochemistry Analyzer, Yellow Springs Instruments Co., Inc.) and 1,3-propanediol was analyzed by HPLC.

TABLE 7

Conversion of 0.2% D-glucose to 1,3-propanediol by
*Escherichia coli* AA200-pKP1-5.
Duplicate reactions were performed[a]

| Experiment | Time (days) | [Glucose] (mM) | [1,3-propane-diol] (mM) | Con. (%) | Sel. (%) |
|---|---|---|---|---|---|
| #1 | 1 | 0.1 | 2.3 | 99 | 21 |
| #1 | 4 | 0.1 | 2.3 | 99 | 21 |
| #2 | 1 | 2.8 | 2.3 | 75 | 28 |
| #2 | 4 | 0.1 | 2.4 | 99 | 21 |

[a]The reactions mixtures, containing trace metals A, were incubated at 37° C.

TABLE 8

Conversion of 1% D-glucose to
1,3-propanediol by *Escherichia coli* AA200-kPA1-5[a]

| time (days) | [glucose] (mM) | [1,3-propane-diol] (mM) | Con. (%) | Sel. (%) |
|---|---|---|---|---|
| 0 | 53 | 0 | 0 | 0 |
| 1 | 39 | 5.6 | 26 | 20 |
| 2 | 35 | 8.3 | 34 | 23 |
| 3 | 33 | 8.4 | 38 | 21[b] |

[a]The reactions mixtures, containing trace metals B, were incubated at 30° C.
[b]At the end of the reaction, the presence of 1,3-propanediol was confirmed by GC/MS and $^{13}$C-NMR (300 MHz).

EXAMPLE 5

Conversion of D-glucose to 1,3-propanediol by *Klebsiella pneumoniae* ECL2106 but not by *Klebsiella pneumoniae* ATCC 25955

Glass serum bottles, filled to capacity (ca 14 mL) with media, were lightly innoculated from a LB agar plate containing *K. pneumoniae* ECL2106 or *K. pneumoniae* ATCC 25955. The media contained 50 mM glucose, 3 mM $(NH_4)_2SO_4$, 0.9 mM $CaCl_2$, 4 µM $CoCl_2$, 0.06 µM $CuCl_2$, 7 µM $FeSO_4$, 2 µM $H_3BO_4$, 0.8 mM $MgSO_4$, 0.2 µM $MnCl_2$, 0.1 µM $Na_2MoO_4$, 0.08 µM $NiCl_2$, 0.3 µM $ZnSO_4$, 0.1 mg/mL DL-cysteine, 10 µM ethylenediaminetetraacetic acid, 0.8 µg/ml vitamin $B_{12}$, potassium phosphate as indicated in Table 9, and either 50 mM HEPES or 50 mM MOPS buffer, pH7.5. The reactions were incubated for 47 hr at 30° C. while shaking at 250 rpm. Otherwise, the reaction was performed as described in Example 1. The results are given Table 9.

TABLE 9

Conversion of D-glucose to 1,3-propanediol by *Klebsiella pneumoniae* ECL2106 but not by *Klebsiella pneumoniae* ATCC 25955

| Strain | Buffer | Pi (mM) | [Glucose] (mM) | [1,3-Propane-diol] (mM) |
|---|---|---|---|---|
| 2106 | MOPS | 5.0 | 11.4 | 0.2 |
| 2106 | MOPS | 2.5 | 13.9 | 0.2 |
| 2106 | MOPS | 1.3 | 14.8 | 0.1 |
| 2106 | MOPS | 0.6 | 15.8 | 0.1 |
| 2106 | HEPES | 5.0 | 21.1 | 0.1 |
| 2106 | HEPES | 2.5 | 23.4 | 0.1 |
| 2106 | HEPES | 1.3 | 26.4 | 0.1 |
| 2106 | HEPES | 0.6 | 27.5 | 0.1 |
| 25955 | MOPS | 5.0 | 4.4 | nd |
| 25955 | MOPS | 2.5 | 5.4 | nd |
| 25955 | MOPS | 1.3 | 2.8 | nd |
| 25955 | MOPS | 0.6 | 7.8 | nd |
| 25955 | HEPES | 5.0 | 7.0 | nd |
| 25955 | HEPES | 2.5 | 13.5 | nd |
| 25955 | HEPES | 1.3 | 10.2 | nd |
| 25955 | HEPES | 0.6 | 17.8 | nd |

What is claimed is:

1. A cosmid contained in ATCC 69789 comprising a DNA fragment of about 35 kb isolated from *Klebsiella pneumoniae* wherein 1) the DNA fragment encodes an active glycerol dehydratase enzyme and 2) digestion of the cosmid results in a restriction digest pattern as shown in FIG. 1, columns 1 and 2.

2. A host bacterium transformed with the cosmid of claim 1.

3. The host bacterium of claim 2 which is deposited with the American Type Culture Collection and having accession number ATCC 69789.

4. A host bacterium comprising the cosmid of claim 1, wherein at least one DNA fragment of said cosmid encodes 1,3-propanediol oxidoreductase, and wherein said host converts a carbon source, other than glycerol or dihydroxyacetone, to 1,3-propanediol.

* * * * *